(12) United States Patent
Lebau

(10) Patent No.: US 11,191,940 B2
(45) Date of Patent: Dec. 7, 2021

(54) SEPTUM ARRANGEMENT

(71) Applicant: Roche Diabetes Care, Inc., Indianapolis, IN (US)

(72) Inventor: Olaf Lebau, Wiesbaden (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 219 days.

(21) Appl. No.: 16/211,617

(22) Filed: Dec. 6, 2018

(65) Prior Publication Data

US 2019/0192841 A1 Jun. 27, 2019

(30) Foreign Application Priority Data

Dec. 22, 2017 (EP) .................................... 17209932

(51) Int. Cl.
*A61M 39/04* (2006.01)
*A61M 39/06* (2006.01)
(Continued)

(52) U.S. Cl.
CPC .......... *A61M 39/045* (2013.01); *A61M 39/04* (2013.01); *A61M 39/06* (2013.01); *A61M 5/142* (2013.01); *A61M 5/158* (2013.01); *A61M 25/06* (2013.01); *A61M 39/0208* (2013.01); *A61M 2039/0036* (2013.01); *A61M 2039/0072* (2013.01); *A61M 2039/066* (2013.01)

(58) Field of Classification Search
CPC .... A61M 39/045; A61M 39/04; A61M 39/06; A61M 2039/0036; A61M 2039/0072; A61M 5/142; A61M 5/158; A61M 25/06; A61M 39/0208; A61M 2039/066; A61M 39/26; A61M 39/0613; A61M 2039/242
See application file for complete search history.

(56) References Cited

U.S. PATENT DOCUMENTS 5,201,714 A * 4/1993 Gentelia ............ A61B 17/3462
251/149.2
2007/0083157 A1 4/2007 Belley et al.
(Continued)

FOREIGN PATENT DOCUMENTS

EP 2 528 642 A2 12/2012
WO WO 93/00129 A1 1/1993
(Continued)

*Primary Examiner* — Lauren P Farrar
(74) *Attorney, Agent, or Firm* — Bose McKinney & Evans LLP

(57) ABSTRACT

Disclosed is septum arrangement having a pierceable septum. The pierceable septum has first and second surfaces positioned opposite to one another and a peripheral surface. A compression element has at least two compression members that partially or fully surround the peripheral surface and has at least two gripping members. Each compression member is connected to at least one gripping member, and the gripping members extend from the compression members towards a common axis (A) which intersects the first surface. A resilient element exerts a biasing force on the pierceable septum that is directed towards the common axis (A). The gripping members define an aperture between them such that introduction of a needle into the aperture exerts a force on the gripping members that counteracts the biasing force and moves the gripping members apart from each other.

10 Claims, 4 Drawing Sheets

(51) Int. Cl.
    *A61M 39/00*     (2006.01)
    *A61M 5/142*     (2006.01)
    *A61M 5/158*     (2006.01)
    *A61M 25/06*     (2006.01)
    *A61M 39/02*     (2006.01)

(56) References Cited

U.S. PATENT DOCUMENTS

| | | |
|---|---|---|
| 2011/0288502 A1 | 11/2011 | Hibdon et al. |
| 2012/0296290 A1 | 11/2012 | Argauer et al. |
| 2016/0317351 A1* | 11/2016 | Ryan .................. A61F 9/00709 |
| 2017/0035992 A1* | 2/2017 | Harding ............ A61M 25/0631 |

FOREIGN PATENT DOCUMENTS

| | | |
|---|---|---|
| WO | WO 00/12171 A1 | 3/2000 |
| WO | WO 01/21251 A1 | 3/2001 |
| WO | WO 02/07804 A1 | 1/2002 |
| WO | WO 2011/060364 A2 | 5/2011 |

* cited by examiner

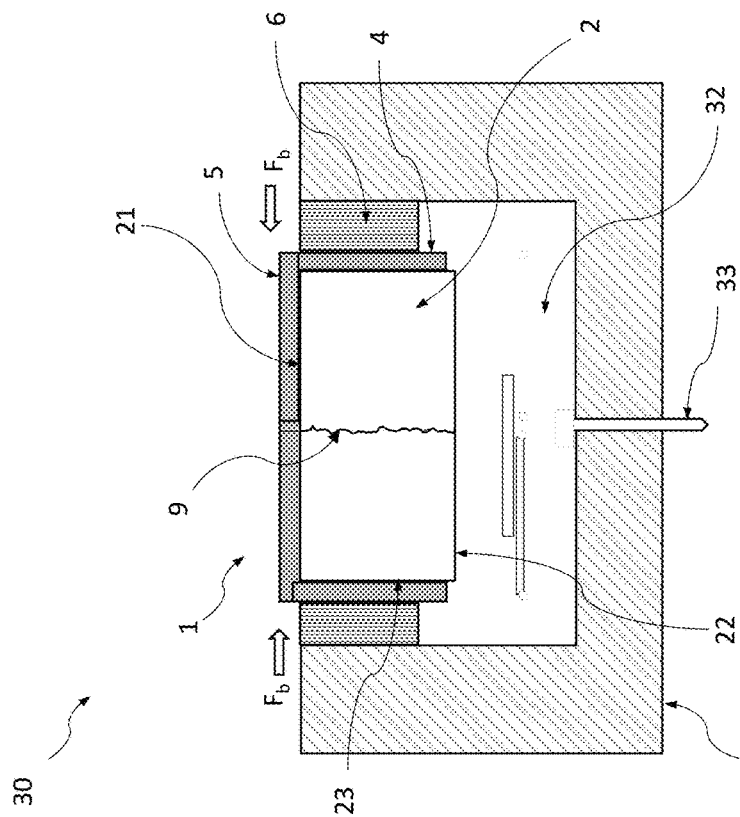
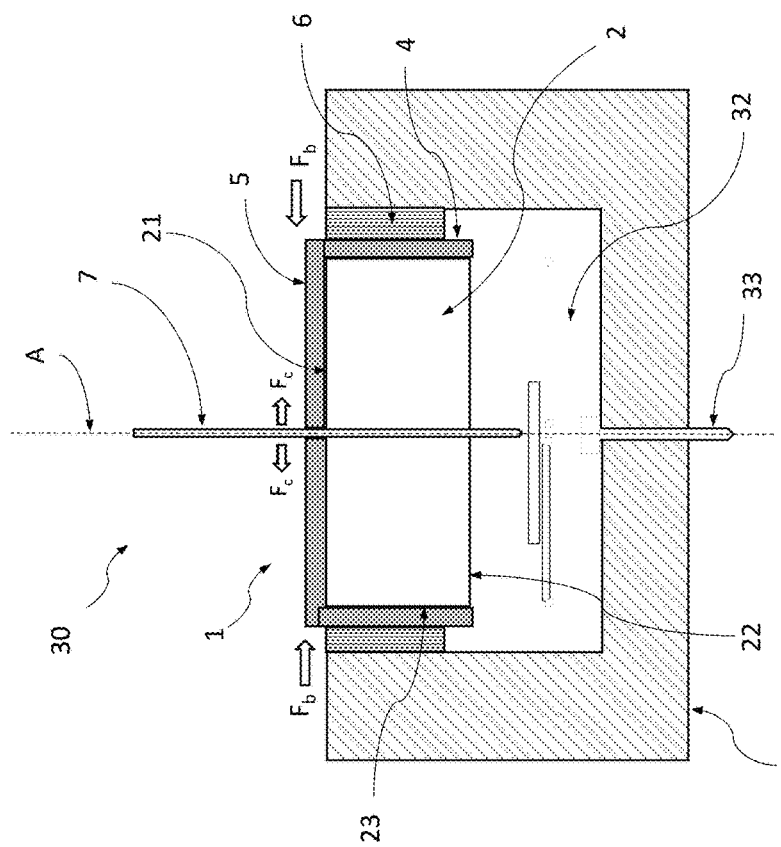

SEPTUM ARRANGEMENT

RELATED APPLICATIONS

This application claims priority to EP 17 209 932.7, filed on Dec. 22, 2017, the entire disclosure of which is hereby incorporated herein by reference.

BACKGROUND

This disclosure lies in the field of infusion or injection technology. More particularly, it is related to arrangements of septa used in infusion sets, to infusion sets or reservoirs comprising a septum arrangement, as well as a method for providing a sealing mechanism with a septum arrangement.

Ambulatory infusion sets are well known in the art. For example, in the therapy of Diabetes Mellitus they are used in combination with a miniaturized infusion pump for Continuous Subcutaneous Insulin Infusion (CSII) where small drug amounts are infused in a metered way via a cannula into the tissue of a patient. Such infusion sets can also be used in a number of further therapies, such as pain therapy or cancer therapy. They are available from a number of suppliers, such as Roche Diabetes Care GmbH, Germany, or Medtronic MiniMed Inc., CA, USA. For example in CSII, the metered doses in the range of microliters or nanoliters.

Although typical infusion sets and infusion systems are usually operated in a continuous manner and thus constantly carried by the patient, there are several daily routines, such as showering, swimming, etc. in which the pump and the tubing should be removed. In such events, it is in the interest of the patient and favorable for cost reasons that the cannula unit remains on the patient so that the flexible infusion cannula used to introduce drug into the patient's tissue is not removed. Therefore, infusion systems have been developed, comprising cannula units which can be easily disconnected from the remaining parts, in particular a tubing, by disconnection of a connector device. The connector device comprises a connector cannula which is fluidly connected to a tubing and an infusion pump. However, upon each reconnection, the septum of the cannula unit is pierced by the connector cannula. As a result, the septum suffers multiple cuts by the commonly employed sharp cannulas and therefore becomes more prone to leakage.

A wide variety of infusion sets for introducing a liquid drug into a patient's body rely on elastic septa, which may be pierced multiple times by a cannula or a needle. A typical infusion set can for example comprise a cannula unit, which can be fluidly connected to an infusion pump and/or a drug reservoir via a tubing with a connector device that has a connector cannula. Typically the cannula unit further comprises a compartment for a liquid drug, which is at least partially formed by a surface of a septum. In particular, the septum may be used for sealing this compartment which is essentially in permanent fluid connection to the patient's tissue via an infusion cannula. In such systems, liquid drug can be transferred to the compartment and subsequently to the patient via the connector cannula and the infusion cannula.

Furthermore, in regard to infusion sets, it is advantageous to employ flexible infusion cannulas for establishing a permanent fluid connection to the patient's tissue. Such flexible infusion cannulas are inserted into the patient's tissue with the help of a piercing needle, such as a rigid steel needle, a section of which is initially arranged within a lumen of the infusion cannula, while a head section is arranged above the septum and the piercing needle penetrates the septum. After insertion of both the piercing needle and the flexible infusion cannula into the tissue, the piercing needle is retracted, while the flexible infusion cannula remains in the tissue. Either a single septum is used for both drug delivery and the introduction of the piercing needle, or alternatively, two different septa may be employed. Typical examples are described in WO 02/07804 A1, U.S. Publication No. 2012/0296290 A1 and EP 2528642 A2.

In order to avoid leakage of the liquid drug, such septa are commonly cylindrically shaped and prestressed by radial compression. A beneficial effect of the radial compression is that after penetration and subsequent removal of the needle or the cannula, the thus generated channel-shaped cut within the septum is compressed and the occurrence of leakage is favorably avoided or at least diminished. Typically, radial compression is achieved during the production process of a cannula unit by crimping the septum into the housing. In a further step, the septum is usually pierced by the piercing needle and the cannula unit is packed and stored in a warehouse, until it is sold and used by a patient.

The crimping process described above causes a permanent compression of the septum. If such a compressed septum is pierced by a needle, the damage caused by the piercing event is significantly larger than in the case of a non-compressed septum. For example, the resulting through cuts are considerably thicker if the septum is compressed. Additionally, during the whole storage time, the septum is permanently deformed by the needle, which may result in a permanent and irreversible deformation after the needle is removed. As a result, leakage becomes a severe problem for septa employed in cannula units as described above.

For the reasons above, septa known in the state of the art can be problematic, in particular with respect to leakage after being kept in a permanently pierced state for long storage times. Firstly, in case of the small dosing units in the nanoliter range, which are typically employed in continuous insulin infusion, any occurring undetected leakage may have a dramatic influence on dosage and thus on the patient's health. Secondly, many automated infusion devices comprise occlusion detection devices which are malfunctioning if operated in an untight system.

SUMMARY

This disclosure improves the state of the art regarding septum arrangements of elastic septa and methods for sealing a septum in the context of infusion and/or injection of liquid drugs, thereby preferably avoiding disadvantages of the prior art fully or partly. The septum arrangement may in particular belong to an infusion set as used, for example, in CSII or to a reservoir for liquid drugs.

In favorable embodiments, the septum arrangement provides a tight sealing by the septum, even if the septum has been permanently pierced by a piercing needle for longer times.

According to an aspect, this disclosure teaches a septum arrangement comprising a pierceable septum with a first surface, a second surface and a peripheral surface. The peripheral surface may be arranged between the first surface and the second surface. In some embodiments, the peripheral surface may comprise edges. The first surface and the second surface are positioned opposite to each other. Additionally, the septum arrangement comprises a compression element. The compression element comprises at least two compression members and at least two gripping members, wherein the at least two compression members partially or fully surround the peripheral surface of the pierceable septum. Each compression member is connected to at least one gripping member. Furthermore, the gripping members extend from the compression members towards a common axis which intersects the first surface. Preferably, the common axis transversely intersects the first surface. The septum arrangement further comprises at least one resilient element. The at least one resilient element exerts a biasing force on the pierceable septum, wherein the biasing force is directed towards the common axis that intersects the first surface. The gripping members define an aperture between them such that introduction of the needle into the aperture exerts a force on the gripping members that counteracts the biasing force and moves the gripping members apart from each other.

According to a further aspect, this disclosure teaches a method for sealing a pierceable septum, comprising the steps (i) introducing a needle into an aperture defined by at least two gripping members, wherein each of the gripping members is connected to at least one compression member which partially or fully surround a peripheral surface of the septum; thereby exerting a force on the at least two gripping members that moves the at least two gripping members apart from each other and that said force counteracts a biasing force, wherein the biasing force is directed towards a common axis intersecting a first surface of the septum and the biasing force is exerted on the pierceable septum by at least one resilient element; (ii) thereafter piercing the septum with the needle; (iii) removing the needle, thereby decreasing the force which is exerted on the gripping members such that the septum is compressed. Preferably, the biasing force in step (i) is exerted on the pierceable septum by the at least one resilient element via at least two compression members.

As used herein, the term "septum" is readily understood by those skilled in the art and is typically an engineered element, for example in the form of a membrane or plug, for sealingly separating a first side and second side in a fluid, i.e., gas and/or liquid, tight seal, which can be pierced by a needle or a cannula. Typically, a septum does not comprise an opening or a puncture, which passes through the septum from the first side to the second side, before a needle or a cannula has been pierced through the septum. Consequently, a stump needle cannot be easily pierced through the septum without exerting high forces. The first and second surfaces may essentially be coplanar.

As readily understood by those skilled in the art, the expression "a force acting towards an axis" is to be understood as a positive force vector, which has a component directed towards an axis, as opposed to a force acting away from an axis. Furthermore, it is clear to the skilled person, that a biasing force that is exerted on the pierceable septum is exerted when no needle is introduced into the aperture. In the pierced state, i.e., in a state in which a needle is introduced into the aperture, no biasing force or at least a diminished force is exerted on the pierceable septum.

In some typical embodiments, the septum is disk-shaped. Moreover, the pierceable septum may have the shape of an, e.g., cylindrical or cuboid plug or may have the shape of a multi-gonal prism, for example a hexagonal prism or a pentagonal prism. In a typical disk-shaped septum, the diameter of the first surface and the second surface is 0.5 mm to 5 mm, preferably 1 mm to 2 mm.

In a typical embodiment, the thickness of the septum, i.e., the distance between the first surface and the second surface, is 0.5 mm to 3 mm, preferably 1 mm to 2 mm.

Advantageously, the pierceable septum is made of a polymer, preferably an elastic polymer or rubber such as silicone, natural rubber, urethane, or any other type of polymer which has the desired physical and chemical properties.

In an embodiment, the biasing force which is exerted by the at least one resilient element on the pierceable septum is a radial force. The radial force may be directed from the compression members to the common axis intersecting the first surface. Preferably the radial force may be directed towards the center of the first surface.

Typically, the at least two compression members may be connected to the at least one resilient element. Alternatively, the gripping members may be connected to the at least one resilient element. In specific embodiments, both the at least two compression members and the at least two gripping members may be connected to the at least one resilient element.

In some embodiments, the compression element comprises two compression members and two gripping members. Preferably, the gripping members may be positioned opposite to each other.

Optionally, the at least two compression members may be configured as an integrally formed resilient ring. Such a resilient ring may fully surround the peripheral surface of the pierceable septum.

In a further embodiment, the resilient element is an elastomer element, such as a rubber element. Alternatively, the resilient element may be a spring, such as a coil spring. If the septum arrangement comprises more than one resilient element, it is clear to the skilled person that the disclosure above also includes the combination of different resilient elements. As readily understood by the skilled person, a suitable resilient element in accordance to the disclosure may be a resilient element that is able to store and release deformation energy.

Furthermore, the at least two compression members and the at least two gripping members may be made from metal or a metal alloy, for example steel, cooper or iron, or from a polymeric material, preferably a thermoplastic or elastic material.

According to a further aspect, this disclosure teaches an infusion set which comprises a septum arrangement according to the present disclosure. The infusion set may comprise a cannula unit with a compartment, which is at least partially formed by the second surface of the septum and is configured to comprise a liquid drug. The compartment can be fluidly connected or temporarily fluidly connected to the patient's tissue via a rigid or soft infusion cannula. Typically, a soft cannula is introduced into the tissue with the help of a rigid piercing needle. The rigid piercing needle is introduced into the aperture defined by the gripping members and pierced through the septum and then introduced into the patient's skin. While such an arrangement is in principle known in the art, the use of a septum arrangement in accordance with this disclosure is particularly favorable in this context since it allows to maintain the septum of the cannula unit pierced by a needle for longer time, for example long storage time in warehouses, wherein the septum is not exposed to any or at least not to any significant compression forces. Thereby, the damage of the septum caused by piercing events can be diminished. Additionally, irreversible deformation of the septum can be avoided or at least reduced. The compression of the septum after removal of the piercing needle further avoids or at least reduces the occurrence of septum leakages.

According to still a further aspect, this disclosure teaches a drug reservoir, for example an insulin cartridge or a drug bag, which comprises a septum arrangement according to this disclosure. The reservoir can, apart from the design of the septum arrangement, be a commonly employed insulin cartridge as known in the art or customly manufactured.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein:

FIG. 6a shows a cross-sectional view of a septum arrangement built into a cannula unit in accordance to another embodiment;

FIG. 6b shows a cross-sectional view of a septum arrangement built into a cannula unit in accordance to another embodiment.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1B:
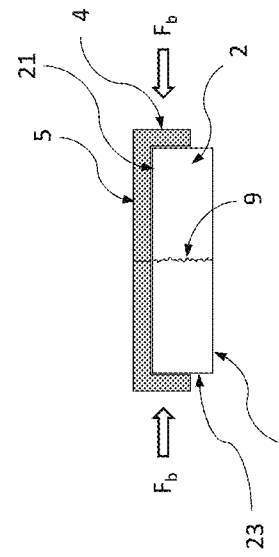
FIG. 1b shows a plan view of a septum arrangement according to another embodiment.
Figure 1A:
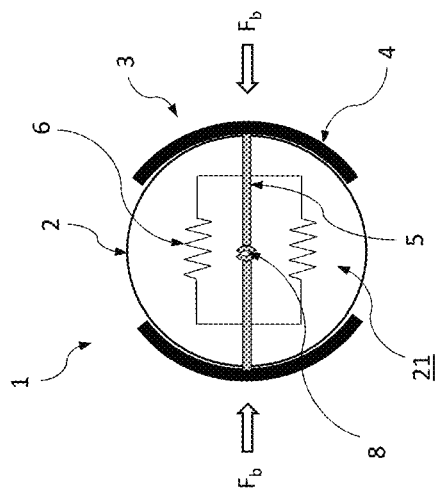
FIG. 1a shows a plan view of a septum arrangement according to one embodiment.

An advantageous embodiment of a septum arrangement 1 is shown in FIG. 1a. The septum arrangement 1 comprises a pierceable septum 2, with a first surface 21 as well as a compression element 3 with compression members 4 and gripping members 5. As can be readily seen, the gripping members 5 extend from the compression members towards a common axis A (shown in FIG. 2a) that intersects the first surface. In the particular embodiment shown, the two gripping members 5 are further positioned opposite to each other. The septum arrangement 1 depicted in FIG. 1 further comprises a resilient element 6, which is designed such that a biasing force $F_b$ is directed towards the common axis A that intersects the first surface. A needle 7 is introduced in the aperture 8 (shown in FIG. 1b), defined by gripping members 5, which causes the exertion of a force $F_c$ that counteracts the biasing force $F_b$ and moves the gripping members 5 apart from each other. As a consequence, the septum 2 is not significantly compressed or the compression is at least significantly decreased when a needle 7 is introduced into the aperture.

FIG. 1b depicts septum arrangement 1 shown in FIG. 1a, however in the absence of needle 7. The resilient elements 6 exert a biasing force $F_b$ on the pierceable septum 2. The biasing force $F_b$ is directed towards the common axis A that intersects the center of the first surface. As a result, force $F_b$ causes the compression elements 3 with gripping members 5 and compression members 4 to move towards each other. In the event, compression members 4 may transfer the biasing force $F_b$ on septum 2, which entails compression and tight sealing of the septum. In the particular embodiment shown, the septum 1 is radially compressed by compression members 4. Furthermore, aperture 8 is depicted in FIG. 1b, which is defined by gripping members 5.

Figure 2B:
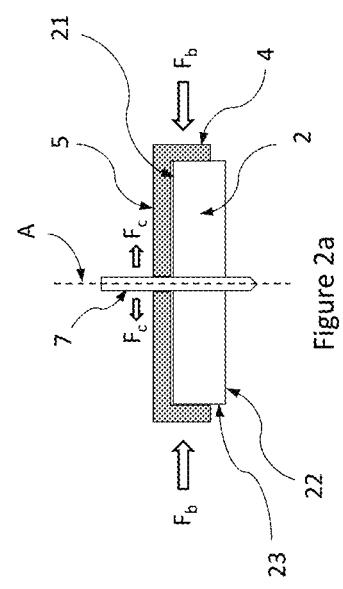
FIG. 2b shows a the cross-sectional view of a septum arrangement according to another embodiment.
Figure 2A:
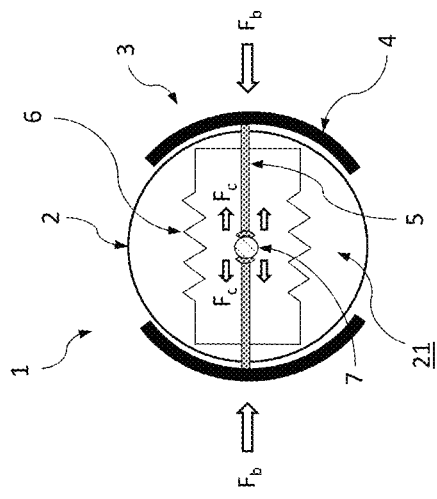
FIG. 2a shows a cross-sectional view of a septum arrangement in accordance with an embodiment.

FIG. 2a shows a schematic cross-sectional view of a septum arrangement 1 according to this disclosure. A needle 7 is introduced into the aperture defined by gripping members 5 and pierced through septum 2. The pierceable septum 2 comprises first surface 21, second surface 22 and peripheral surface 23. As can be readily seen, peripheral surface 23 is arranged between first surface 21 and second surface 22. As already described above (see description of FIG. 1a), a resilient element 6 is designed such that a biasing force $F_b$ is directed towards a common axis A that intersects the first surface 21. Gripping members 5 define an aperture 8 (shown in FIG. 1b) such that the introduction of needle 7 into the aperture exerts a force $F_c$ on the gripping members that counteracts the biasing force $F_b$ and moves the gripping members apart from each other. As a result, the compression of elastic septum 2 is at least significantly decreased, for example such that the septum may expand in the lateral direction, that is transverse to axis A. In FIG. 2a, the axis A is transversely arranged to first surface 21.

FIG. 2b shows the septum arrangement 1 of FIG. 2a, however, the needle 7 has been removed. As a result of the removal of the needle, septum 2 features through cut 9. Due to the removal of the needle, the resilient element 6, exerts a biasing force $F_b$ on the pierceable septum, for example via compression members 4, i.e., the force $F_b$ leads to compression of septum 1 in the lateral direction as gripping members 5 are moved towards each other. As a consequence of the compression, the through cut 9 is sealingly closed and thus the occurrence of leakage is avoided or at least diminished.

Figure 3B:
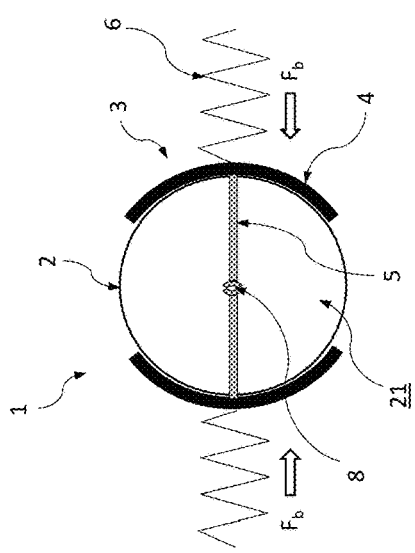
FIG. 3b shows a plan view of a septum arrangement according to another embodiment.
Figure 3A:
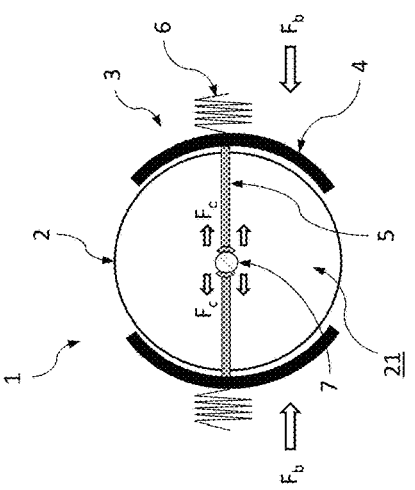
FIG. 3a shows a plan view of a septum arrangement in accordance to another embodiment.

FIG. 3a depicts another embodiment of a septum arrangement 1 in accordance to this disclosure. In this embodiment, the septum arrangement 1 comprises two resilient elements 6, which may be either springs, such as coil springs, or elastomer elements. As can be seen, each of the two compression elements 3 is connected to one resilient element 6. The resilient elements 6 are designed such that a biasing force $F_b$ is exerted that is directed towards a common axis that intersects the first surface 21 of the septum 2.

FIG. 3b shows the septum arrangement 1 of FIG. 3a in the absence of the needle 7, for example after removal of the needle 7. Due to the removal of the needle, the gripping members 5 move towards each other and force $F_b$, which is caused by the resilient elements 6, is exerted on the pierceable septum 2 via compression members 4.

Figure 4:
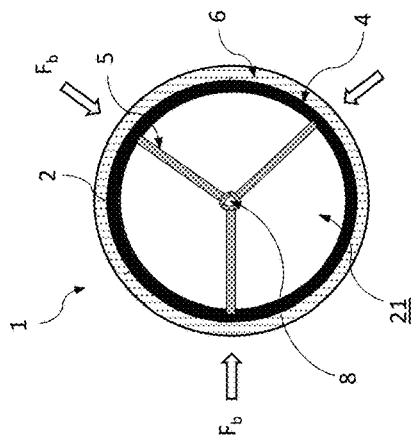
FIG. 4 shows a plan view of the septum arrangement in accordance to another embodiment.

FIG. 4 shows a further embodiment of a septum arrangement 1 according to this disclosure with three compression elements. The compression elements essentially fully surround the peripheral surface of the septum 2. Each compression element comprises a gripping member 5 and a compression member 4. The septum arrangement depicted further comprises one resilient element 6, which is connected to all three compression elements. The particular resilient element shown, may be an elastic element made from rubber or suitable elastomers. Resilient member 6 has a ring shape and exerts a biasing force $F_b$ on the pierceable septum 2, wherein the biasing force $F_b$ is directed towards the common axis A that intersects the center of the first surface 21. As readily understood by those skilled in the art, resilient element 6 can be compressed. The three gripping members 5 define an aperture 8 such that a needle can be introduced and such that upon introduction of the needle into the aperture, a force is exerted that counteracts the biasing force and moves the gripping members 5 apart from each other. During this process, the compression members 4 are pushed against resilient element 6, which leads to a compression of the resilient element. Accordingly, the resilient element may store the respective deformation energy, which may be released upon removal of the needle.

Figure 5:
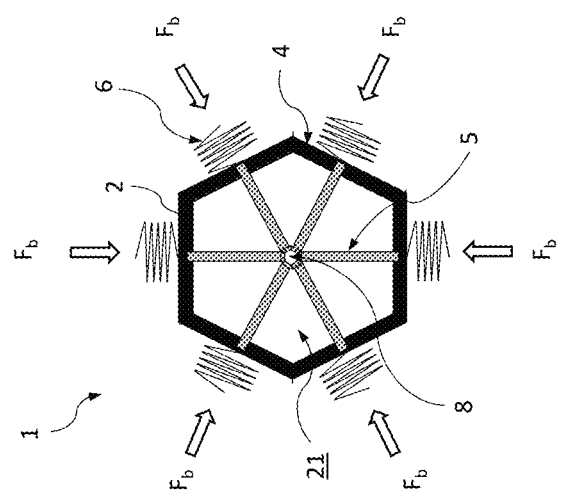
FIG. 5 shows a plan view of the septum arrangement in accordance to another embodiment.

FIG. 5 shows a further embodiment of a septum arrangement 1 according to this disclosure, in which the pierceable septum 2 is a hexagonal prism with a hexagonal first surface 21. Furthermore, the septum arrangement contains six compression elements each comprising one compression member 4 and one gripping member 5. As can be readily seen, each compression member 4 is connected to one resilient element 6. However, as the skilled person understands, the resilient elements can also be integrally formed as one resilient element as shown in FIG. 4.

FIG. 6a depicts a septum arrangement 1 according to this disclosure, which is built into housing unit 31. The housing unit 31 is part of a cannula unit 30, which itself may be part of an infusion set. Additionally, cannula unit 30 may comprise flexible cannula 33, which may be inserted into the patient's tissue by introduction of piercing needle 7 into the aperture that is defined by gripping members 5, and piercing of septum 2. As can be readily seen, the cannula unit 30 comprises compartment 32, which can contain a liquid drug. The septum arrangement 1 comprises pierceable septum 2 with first surface 21, second surface 22 and peripheral surface 23. The peripheral surface 23 is positioned between the first surface and the second surface and can for example be the shell surface of a cylindrical septum. Furthermore, the first surface 21 and the second surface 22 are positioned opposite to each other. The septum arrangement 1 further comprises two compression elements with compression members 4 and gripping members 5. The gripping members 5 extend from the compression members towards a common axis A which intersects the first surface. Additionally, the septum arrangement comprises resilient element 6, which exerts a biasing force $F_b$ on the pierceable septum 2, wherein the biasing force is directed towards the common axis A that intersects the center of the first surface. The gripping members 5 define an aperture between them such that introduction of the needle 7 into the aperture exerts a force $F_c$ on the gripping members that counteracts the biasing force and moves the gripping members 5 apart from each other.

FIG. 6b shows cannula unit 30 with septum arrangement 1, built into housing unit 31. However, the piercing needle (see 7 in FIG. 6a) has been removed. As indicated by the curved line, the removal of the needle led to the formation of through cut 9 in septum 2. This through cut is now sealingly closed, as the removal of the needle leads to expansion of resilient element 6 with concomitant exertion of biasing force $F_b$ thus compressing the septum, preferably by radial compression.

Figure 7:
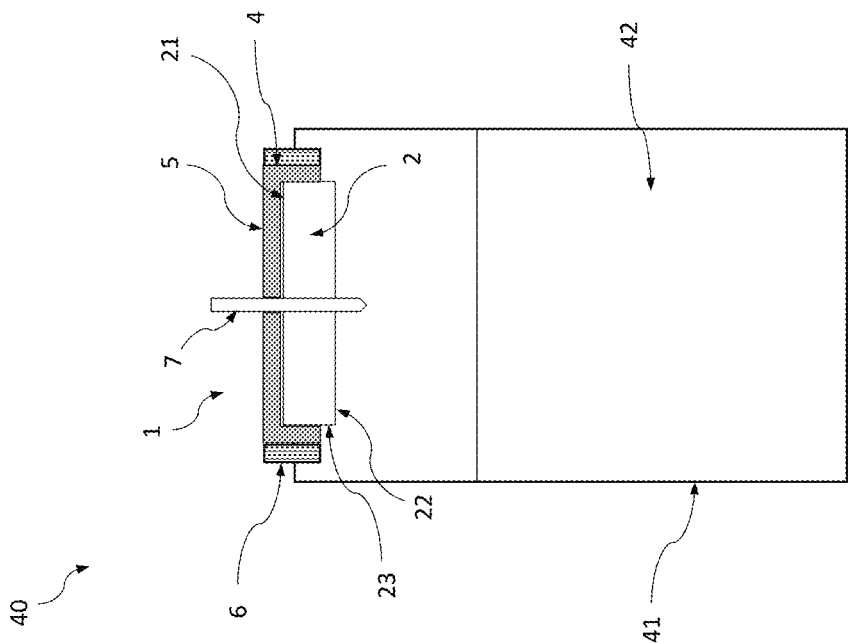
FIG. 7 shows a cross-sectional view of a septum arrangement built into a reservoir for a liquid drug in accordance to another embodiment.

FIG. 7 depicts a reservoir for drugs 40, for example an insulin cartridge comprising walls 41 and liquid drug 42. A septum arrangement 1 according to this disclosure allows to withdraw drug 42 from the reservoir by cannula 7 and ensures tight sealing of the pierced septum 2 after removal of the cannula.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. A septum arrangement, comprising:
   a pierceable septum having a first surface and a second surface positioned opposite to one another and a peripheral surface;
   a compression element having at least two compression members that partially or fully surround the peripheral surface and having at least two gripping members, wherein each compression member is connected to at least one of the gripping members, and wherein the gripping members extend from the compression members towards a common axis (A) which intersects the first surface;
   a resilient element that exerts a biasing force on the pierceable septum, wherein the biasing force is directed towards the common axis (A);
   wherein the gripping members define an aperture between them whereby introduction of a needle into the aperture exerts a force on the gripping members that counteracts the biasing force and moves the gripping members apart from each other; and
   wherein the introduction of the needle results in the piercing of the septum creating a through cut extending through a thickness of the septum from the first surface to the second surface and wherein, upon removal of the needle, the biasing force sealingly closes the through cut.

2. The septum arrangement according to claim 1, wherein the biasing force is a radial force.

3. The septum arrangement according to claim 1, wherein the at least two compression members and/or the at least two gripping members are connected to the resilient element.

4. The septum arrangement according to claim 1, wherein the at least two gripping members comprises two gripping members positioned opposite to each other.

5. The septum arrangement according to claim 1, wherein the at least two compression members are configured as an integrally formed resilient ring.

6. The septum arrangement according to claim 1, wherein the resilient element is an elastomer or a spring.

7. The septum arrangement according to claim 1, wherein the at least two compression members and the at least two gripping members are made from metal or a metal alloy, or from a polymeric material.

8. An infusion set comprising a septum arrangement according to claim 1.

9. A reservoir for a liquid drug comprising a septum arrangement according to claim 1.

10. A septum arrangement, comprising:
    a pierceable septum having a first surface and a second surface positioned opposite to one another and a peripheral surface;
    a compression element having at least two compression members that partially or fully surround the peripheral surface and having at least two gripping members, wherein each compression member is connected to at least one of the gripping members, and wherein the gripping members extend from the compression members towards a common axis (A) which intersects the first surface;

a resilient element that exerts a biasing force on the pierceable septum, wherein the biasing force is directed towards the common axis (A);

wherein the gripping members define an aperture between them whereby introduction of a needle into the aperture exerts a force on the gripping members that counteracts the biasing force and moves the gripping members apart from each other; and wherein the first and second surfaces of the septum are parallel with each other and separated by a thickness of the septum.

\* \* \* \* \*